United States Patent [19]

Cook et al.

[11] 4,337,775
[45] Jul. 6, 1982

[54] CATHETER DRAINAGE AND PROTECTION UNIT

[75] Inventors: Yale B. Cook, Sun Valley; Charles R. Brooks, Manhatten Beach, both of Calif.

[73] Assignee: Irving Levine, Calabassas, Calif.

[21] Appl. No.: 209,840

[22] Filed: Nov. 24, 1980

[51] Int. Cl.³ ............................................ A61M 25/00
[52] U.S. Cl. ................................................ 128/349 B
[58] Field of Search ............... 128/295, 349 R, 349 B, 128/349 BV, 350 R, 348

[56] References Cited

U.S. PATENT DOCUMENTS

| | | | |
|---|---|---|---|
| 2,213,210 | 12/1940 | Egbert | 128/349 |
| 2,547,758 | 4/1951 | Keeling | 128/349 B |
| 2,547,758 | 7/1951 | Keeling | 128/349 |
| 3,154,080 | 3/1964 | Rowan et al. | 128/349 |
| 3,605,752 | 9/1971 | Schlesinger | 128/349 |
| 3,630,206 | 12/1971 | Gingold | 128/349 B |
| 3,769,981 | 11/1973 | McWhorter | 128/349 B |
| 3,982,544 | 9/1976 | Dyck | 128/349 R |
| 4,116,227 | 5/1978 | Eisenberg et al. | 128/349 |
| 4,237,894 | 12/1980 | Cohen | 128/349 R |

Primary Examiner—Dalton L. Truluck
Attorney, Agent, or Firm—Michael A. Painter

[57] ABSTRACT

A catheter drainage and protection unit for venting urine drainage and collecting urine samples while preventing inadvertent spillage of urine due to overflow. A slender cannula is entered longitudinally of the penis in the urethra, the distal end thereof reaching into the male bladder. A foley catheter integral with the distal end of the cannula is inflated by appropriate medicinal fluid to prevent dislodgement of the catheter from the bladder. A flexible cap is disposed about the head of the penis circumscribing the cannula, the narrow outlet of the flexible cap being coupled about one branch of a tube leading to a flexible collection container. The cannula exits the flexible cap in a concentric relationship therewith entering the end portion of a first branch of the drainage tubing. The cannula passes through an aperture in the first branch of the drainage assembly and is coupled to a second branch of the drainage tubing thereby providing for full drainage from the male bladder through the cannula as well as any fluid which may escape from the urethra about the exterior of the cannula.

4 Claims, 3 Drawing Figures

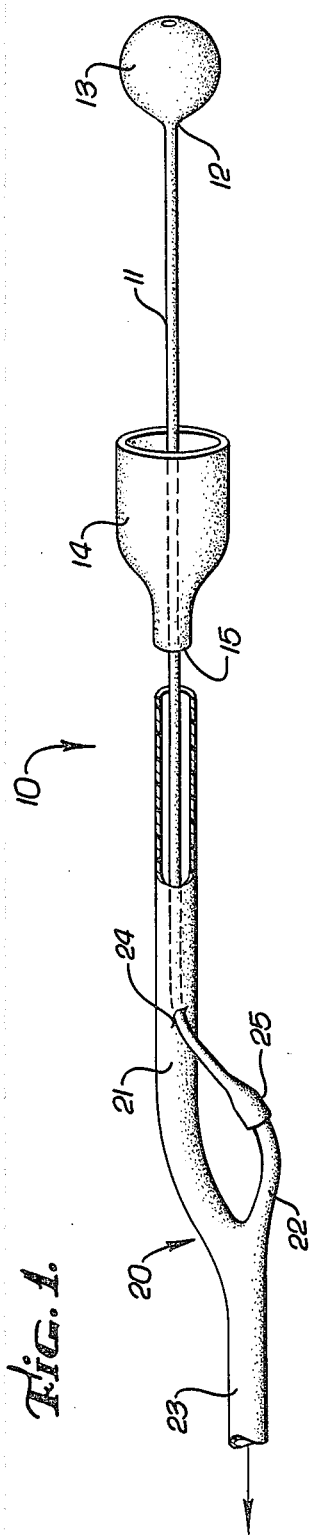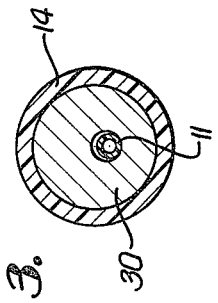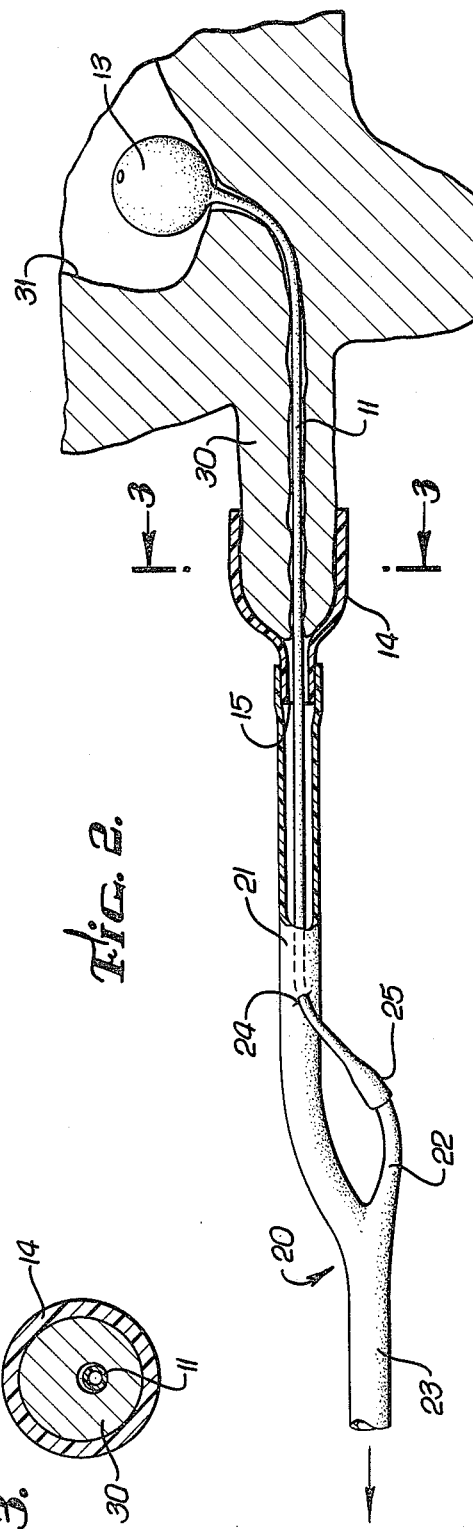

CATHETER DRAINAGE AND PROTECTION UNIT

BACKGROUND OF THE INVENTION

1. Field of the Invention

The present invention generally relates to a device for draining liquid from the male bladder and, more particularly, to devices for preventing liquid from being discharged which may inadvertently escape from the urethra about an inserted cannula.

2. Prior Art

Urine drainage systems are utilized when patients do not have any voluntary control over their urination, making it necessary for a uretheral catheter to be extended into the patient's bladder. The outlet end of the catheter is then directly or indirectly connected to a suitable urine collection reservoir, such as a flexible bag or the like, into which the urine drains by gravity. Even when the patient is not urinating, a column of previously collected urine can build up within the urine drainage system, which column creates a suction at the inlet end of the catheter which can cause the bladder to prolapse about the catheter tip. This can cause lesions to develop in the bladder musoca. In addition, even where a catheter is extended into the patient's bladder, urine can escape from the urethra about the outer wall of the catheter or cannula thereby soling the patient's clothing, bedding, etc.

Medical science dictates that a system of drainage be provided from the interior of a body space to the exterior, and since such means of drainage cannot be accomplished by normal physiological routes, an artificial conduit or catheter must be employed. The catheter is passed through the urethra into the urinary bladder. In addition to supplying urinary drainage, the catheter system must provide for drainage and collection of inflammatory products within the plueral cavity while simultaneously avoiding inadvertent spillage which can be unsanitary as well as unhealthy.

One of the devices disclosed by the prior art comprises a urinary drainage system which employs a venting adaptor unit which employs a bacteria and liquid impermeable filter. A mid-stream urine collector adaptor unit is provided which includes a body preferably made of synthetic plastic material and having an outer annular recessed portion into which opens a urine collection port. The problem inherent in this device relates to its inability to collect drainage which may pass through the urethra but not about the catheter. Irrespective of the venting system, conditions can occur whereby urine or other drainable fluids will not be appropriately collected.

Another device taught by the prior art employs a cap which is disposed about the end of the penis. Rather than providing for a secure drainage system, this unit provides for insertion of medicinal fluids thereby totally avoiding a primary objective of the present invention. The present invention employs a slender cannula or catheter which is inserted through the urethra into the patient's bladder. The distal end of the cannula which is disposed within the bladder is inflated by appropriate medicinal fluid to prevent inadvertent dislodgement of the catheter. A flexible cap is disposed about the end of the penis enveloping the cannula in a concentric relationship as it exits the penis. The exit port of the cap as well as the cannula are coupled to respective branches of a drainage canal which empty into an appropriate drainage reservoir. By preventing urine or other fluid from escaping which may exit the urethra external to the catheter, the deficiencies inherent in the devices taught by the prior art are overcome.

SUMMARY OF THE INVENTION

The present invention catheter drainage and protection unit comprises three basic subsystems: (1) a uretheral catheter or cannula which is inserted through the male urethra into the patient's bladder; (2) the central drainage system and container; and (3) the protective cap used for preventing inadvertent leakage of urine or other fluid discharge beyond the confines of the system. The uretheral catheter or cannula is a flexible, slender tube which is inserted through the male urethra and into the urinary bladder. The distal end of the catheter is expandable and can be injected with appropriate medicinal fluids to expand the end thereof to prevent dislodgement of the catheter. The cannula extends from the end of the penis into one branch of the drainage system. A flexible cap is disposed about the end of the penis forming a fluid tight seal therewith. The cannula is concentrically disposed through the exit port of the cap and into a branch of the drainage system. The drainage system comprises a Y-shaped tubing, one branch thereof being coupled to the exit port of the cap, the other branch thereof being coupled to the output of the cannula.

Since the urine drainage system is to be utilized when patients have no control over urination, the uretheral catheter will drain all urine or other fluid discharge directly into one branch of the drainage system. Since fluid can escape about the outer surface of the cannula, the cap which is adjusted to engage the head of the penis prevents inadvertent discharge of the fluid beyond the confines of the system. Any fluid which manages to pass through the uretheral canal outside of the uretheral catheter will be trapped by the engaged field formed by the cap about the head of the penis and be directed through the alternative branch of the drainage system.

It is therefore an object of the present invention to provide an improved catheter drainage and protection system.

It is another object of the present invention to provide a more compact and durable means for maintaining the integrity of a urine drainage system.

It is still another object of the present invention to provide a catheter drainage system which will prevent inadvertent discharge of fluids beyond the confines of the system.

It is still yet another object of the present invention to provide a catheter drainage and protection system which is simple and inexpensive to fabricate.

The novel features which are believed to be charastic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only and is not intended as a definition of the limits of the invention.

BRIEF DESCRIPTION OF THE DRAWINGS

FIG. 1 is an elevation view in partial cross-section of the present invention catheter drainage and protection unit.

FIG. 2 is an elevational view of the present invention catheter drainage and protection unit mounted within the male uretheral canal.

FIG. 3 is a cross-sectional view of the cap and cannula taken through line 3—3 of FIG. 2.

DESCRIPTION OF THE PRESENTLY PREFERRED EMBODIMENT

The present invention catheter drainage and protection unit can be best seen by reference to FIG. 1 wherein an assembly view of the entire unit is shown generally designated by the reference numeral 10. As stated, urine drainage systems are utilized when patients do not have any voluntary control over urination making it necessary for an uretheral catheter to be extended into the patient's bladder. The outlet end of the catheter is then directly or indirectly connected to a suitable urine collection reservoir such as a flexible bag or the like into which urine drains by gravity. As will be described hereinbelow, all aspects of the assembly of the present invention are shown with the exception of the urine reservoir which can be any conventional bag or like container.

A slender catheter or cannula 11 is used as the conduit for the fluid drainage from the patient's bladder. The cannula is fabricated of soft flexible plastic or a latex medical grade tubing which is well known in the industry. At the distal end 12 of cannula 11 is formed an expandable member 13 which typically forms a unit commonly known as a foley catheter. Expandable member 13 is intended to be placed within the patient's bladder, cannula 11 extending from the head of the patient's penis. Flexible cap 14 is adapted to be disposed about and engage the head of the penis in such a manner as to be periodically replaceable as required by the circumstances of the patient's condition. Exit port 15 of cap 14 circumscribes cannula 11 as it is output from the head of the patient's penis.

The drainage and disposal system comprises a Y-shaped section 20 having branches 21 and 22 to provide for the fully enclosed urine drainage system. The junction of branches 21 and 22 provide for passage to the disposal reservoir via tube 23, the drainage reservoir not being shown. The present invention is assembled by creating an aperture 24 through the wall of branch 21 through which cannula 11 is disposed. The end 25 of cannula 11 is engaged with branch 22 to provide for a contiguous path from the expanded member of the foley catheter 13 through tube 23 to the reservoir bag.

The operation of the present invention can be best seen by reference to FIGS. 2 and 3. As stated hereinabove, an objective of the present invention is to create a fully sealed, closed system for the passage of urine or other fluids being drained from a patient's bladder. As can be seen in FIG. 2, cannula 11 is disposed through the urethra of penis 30 into bladder 31. In order to secure the catheter in place, expanded member 13 is filled with medicinal fluid such as water. Approximately 5 cubic centimeters will typically be sufficient to insure that cannula 11 is not inadvertently dislodged from bladder 31. Cannula 11 extends from the end of penis 30. A flexible cap 14 is manufactured of a resilient material and adjustably engages the head of penis 30. As can be seen best in FIG. 2, terminus 15 of cap 14 circumscribes cannula 11 providing for a passage for urine or other fluids which drain through the urethra and external tube cannula 11. The terminus or exit port 15 is coupled to and firmly engaged within branch 21 of the drainage assembly which has been generally designated by the reference numeral 20. Cannula 11 passes through aperture 24 in branch 20 and is in turn firmly coupled to branch 22. In order to fully seal the system, medical adhesive closes all couplings between terminus 15 and branch 21, the aperture 24 through which cannula 11 is disposed as well as the coupling between cannula 11 and branch 22. Upon the sealing of the unit, the catheter collecting unit is fully self-contained and will provide a system in which inadvertent spillage is eliminated.

The use of the present invention is clearly explained by reference to FIG. 2. Cap 14 is a replaceable unit which can periodically be changed for medical purposes. Once cannula 11 is in place, urine passing through the catheter will exit through branch 22 and into tube 23. In the event any urine or other drainage passes about the exterior of cannula 11 through the urethra, it will be collected within branch 21 external to cannula 11 and be disposed of via tube 23. It can therefore be seen that the present invention comprises an improved catheter system for controlling the disposal of urine and preventing inadvertent spillage of the urine or other draining fluid.

We claim:

1. A catheter drainage and protection unit for draining fluids from the male urethra comprising:
    (a) a cannula having a distal portion adapted for insertion through the male urethra into the bladder, said cannula having a draining end for the drainage of fluid;
    (b) expandable means for securing said cannula in place within the urethra, said expandable means being integral with the distal end of said cannula;
    (c) a flexible cap having an exit port concentrically disposed about the draining end of said cannula and a body engaging portion integral therewith;
    (d) a drainage assembly comprising a central drainage tube and first and second branch tube members in communication with said central drainage tube, said first branch tube being coupled to the exit port of said cap and concentrically receiving the draining end of said cannula therethrough, the draining end of said cannula being disposed through an aperture in the wall of said first branch tube and being coupled to the second branch tube of said central drainage tube; and
    (e) means for sealing the couplings between said cap and cannula, and said central drainage tube.

2. A catheter drainage and protection unit as defined in claim 1 wherein said flexible cap comprises a first cylindrical member adapted for body engagement, said first cylindrical member being integrally tapered into a second cylindrical member of a smaller diameter than said first cylindrical member, said second cylindrical member being coupled to the first branch tube.

3. A catheter drainage and protection unit as defined in claim 2 wherein said cannula is concentric with the second cylindrical member of said cap whereby said fluid draining through the urethra external to the said cannula drains intermediate said second cylindrical member and said cannula.

4. A catheter drainage and protection unit as defined in claim 1 wherein said expandable means comprises an inflatable member adapted to be disposed within the bladder and to receive medicinal fluids for positioning said cannula in place within the urethra.

* * * * *